United States Patent [19]

Shin et al.

[11] Patent Number: 4,554,389

[45] Date of Patent: Nov. 19, 1985

[54] UNSYMMETRICAL DIPHENOLIC COMPOUNDS

[75] Inventors: Kju Hi Shin; Edward F. Tatum, both of Baton Rouge, La.

[73] Assignee: Ethyl Corporation, Richmond, Va.

[21] Appl. No.: 598,058

[22] Filed: Apr. 9, 1984

[51] Int. Cl.$^4$ .............................................. C07C 39/12
[52] U.S. Cl. ..................................... 568/722; 568/723
[58] Field of Search ........................ 568/722, 728, 723

[56] References Cited

U.S. PATENT DOCUMENTS

| | | | |
|---|---|---|---|
| 2,838,571 | 6/1958 | Fibley | 568/722 |
| 3,030,428 | 4/1962 | Morris | 568/722 |
| 3,053,803 | 9/1962 | Jaffe et al. | 568/722 |
| 3,091,645 | 5/1963 | Rocklin | 568/722 |
| 3,211,652 | 10/1965 | Hinkamp | 568/722 |
| 3,761,525 | 9/1973 | Young et al. | 568/722 |

Primary Examiner—Werren B. Lone
Attorney, Agent, or Firm—Donald L. Johnson; John F. Sieberth; John F. Hunt

[57] ABSTRACT

4-[[4-hydroxy-3,5-bis(1-methylethyl)phenyl]hydrocarbyl]-2,6-dimethylphenols.

The compounds of the invention such as 4-[[4-hydroxy-3,5-bis(1-methylethyl)phenyl]hydrocarbyl]-2,6-dimethylphenol have low melting points and other physical and chemical properties making them valuable as curing agents, antioxidants, and for other purposes.

4 Claims, No Drawings

UNSYMMETRICAL DIPHENOLIC COMPOUNDS

BACKGROUND OF THE INVENTION

I. Field of the Invention

This invention relates in general to new aromatic diphenolic (diol) compounds which have various utilities and desirable physical and chemical properties.

II. Description of the Prior Art

Various bisphenols and similar compounds have been made according to processes of the prior art but there exists a need for aromatic diphenolic compounds having desirable properties for a variety of uses.

CROSS-REFERENCE

Reference is made to co-pending application Ser. No. 598,225, filed Apr. 9, 1984, in the name of Kju Hi Shin. Said application and this application are commonly assigned.

SUMMARY OF THE INVENTION

The present invention is directed to providing compounds having good physical properties for various utilities, said compounds being of a particular unsymmetrical structure which has been found to impart desirable physical and chemical properties. The present invention comprises compounds of structure I:

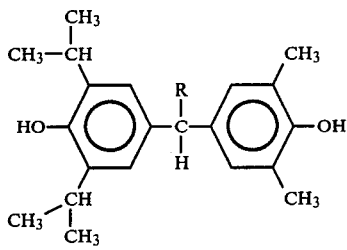

wherein R is H or a radical selected from the group consisting of alkyls, alkenyls, cycloaliphatics, aromatics, heteroatomics, and heterocyclics. The alkyls and alkenyls are preferably 1–7 carbon atoms. The cycloaliphatics are preferably 3–7 carbon atoms. The aromatics are preferably 6–10 carbon atoms. The heterocyclics are preferably 5–7 member rings. The heteroatomics preferably contain 1–7 atoms other than hydrogen usually carbon and oxygen.

The compounds of the present invention are usable as diol chain extenders for reaction with organic polyols and organic polyisocyanates to form polyurethanes having a broad scope of application. The compounds of the present invention are also usable as antioxidants to protect organic materials including hydrocarbon lubricating oils and polyolefins. The compounds of the present invention are also usable as curing agents for epoxies and the like or as intermediates for synthesis of a variety of end products. The most preferred compound of the present invention is 4-[[4-hydroxy-3,5-bis(1-methylethyl)phenyl]methyl]-2,6-dimethylphenol which may also be denominated as [3,5-diisopropyl-4-hydroxyphenyl] [3',5'-dimethyl-4'-hydroxyphenyl] methane, 4-[[4-hydroxy3,5-diisopropylphenyl]methyl]-2,6-dimethylphenol, 2,6-diisopropyl4-(3,5-dimethyl-4-hydroxybenzyl)phenol or 4-(2,6-diisopropyl-4-hydroxybenzyl)-2,6-xylenol.

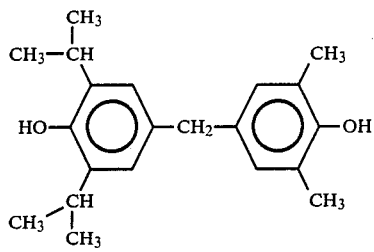

This compound is preferred because it has a low melting point and other desirable physical and chemical properties for chain extender, antioxidant, and other uses.

DESCRIPTION OF THE PREFERRED EMBODIMENT

The present invention provides compounds of structure I:

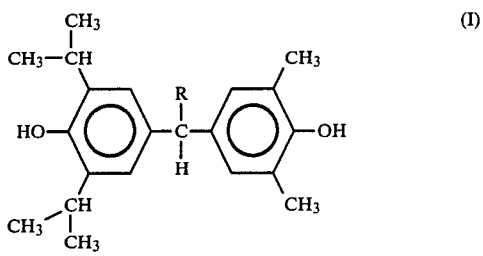

wherein R is H, alkyl, alkenyl, cycloaliphatic, aromatic, heteroatomic, or heterocyclic.

The compounds of the present invention have two phenolic moieties with methyl substituents in the two positions ortho to the hydroxyl group of one phenolic moiety and isopropyl substituents in the two positions ortho to the hydroxyl group of the other phenolic moiety. These phenolic moieties are bridged by a divalent group to form the compounds of the invention which because of the unsymmetrical positioning of the isopropyl and methyl substituents relative to the two phenolic moieties and the symmetrical positioning of the isopropyl and methyl substituents on the individual phenolic moieties have good physical and chemical properties for both reactivity and stability in their intended uses.

The compounds of the invention may be synthesized by two methods. The preferred methylene-bridged compound of the invention may be prepared from (2,6-diisopropyl-4-hydroxybenzyl) (hydrocarbyl) ethers by reacting such an ether with 2,6-dimethylphenol in the presence of a strong acid such as $H_2SO_4$ at about 0°–10° C., preferably 0°–5° C. The precursor ethers may be obtained by the process of Filbey, U.S. Patent No. 2,838,571 which is incorporated herein by reference.

The compounds of the invention generally may be obtained by a process disclosed in commonly assigned copending application Ser. No. 598,225, filed Apr. 9, 1984 According to that process 2,6-dimethylphenol or 2,6-diisopropylphenol is added (preferably gradually) to a refluxing solvent portion of an alcohol with a secondary amine and an aldehyde. The aldehyde is of the type RCHO wherein R is as set forth above.

The divalent radical

attaches at the para position of the phenol and an ether of structure II is formed:

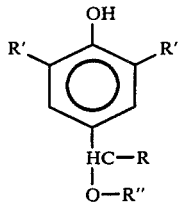

where the R' are either both methyl or both isopropyl, the R" is a hydrocarbyl group (preferably alkyl) provided from the alcohol and R is as set forth above for the bridging group. The ether is then reacted with 2,6-diisopropylphenol or 2,6-dimethylphenol as required to make a novel compound of the invention. Thus the choice of aldehyde used to make the precursor ether determines the divalent bridging group of the compounds of the invention.

Most aldehydes are suitable for use according to the invention but those with twelve or fewer carbon atoms are more readily used to make the ethers of structure II. Those with eight or fewer carbon atoms are more preferred. The aldehydes usable with the invention include formaldehyde, acetaldehyde, butyraldehyde, benzaldehyde, benzylaldehyde, propionaldehyde, benzalacetaldehyde (cinnamaldehyde—($C_6H_5$)CH= CH—CHO), cuminicaldehyde (($CH_3$)$_2$CH ($C_6H_4$)CHO or para-isopropylbenzaldehyde), heptylic aldehyde, furfuraldehyde, crotonaldehyde, and glyoxalic acid and its esters.

The phenolic groups of the compounds of the invention are bonded to the same carbon atom which is part of the divalent radical bridge. That is the divalent radical from the aldehyde always bridges the phenolic moieties across a single carbon atom.

Accordingly, the divalent radicals which bridge the phenolic moieties include furfurylidene, propenylidene, benzylidene, β-phenethylidene

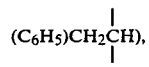

methylene, ethylidene, propylidene, butylidene, isobutyrilidene, cyclohexylmethylene, 2,2-dimethylpropylidene, propenylidene

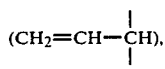

and the divalent radicals from glyoxalic acid and its esters such as

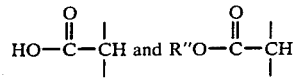

wherein the R" is a hydrocarbyl radical. The radical

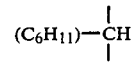

may be obtained by hydrogenation of benzaldehyde prior to use in the production of the ethers of structure II.

From the above it is clear that the R of structures I and II may, among other radicals, be alkyls such as methyl, ethyl, propyl, isopropyl, n-butyl, isobutyl, sec-butyl, n-hexyl, and the like; cycloaliphatics such as cyclohexyl or cyclopentyl; aromatics such as phenyl, benzyl or cumyl; heterocyclics such as the monovalent furan radical from fufurylidene; heteroatomics such as the radicals

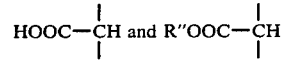

from glyoxalic acid and its esters; and alkenyls such as ethenyl, propenyl, and the like.

It can be seen that the compounds of the invention have the phenolic moieties bonded to the same carbon atom.

According to the invention, stablized organic compositions are provided which contain a compound of structure I of the invention.

The compounds of the invention can be used as antioxidants in a broad range of organic material normally subject to gradual degradation in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding additives nor flame suppressing additives and the degradation protected against is not combustion but, rather, the gradual deterioration of the organic composition due to the effects of oxygen over an extended period of time.

Examples of organic materials in which the additives are useful include polymers, both homopolymers and copolymers, of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additives provide antioxidant protection in natural and synthetic rubbers such as copolymers of olefinically unsaturated monomers including styrene-butadiene rubber (SBR rubber), ethylene-propylene copolymers, ethylene -propylenediene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise acrylonitrile-butadiene-styrene (ABS) resins are effectively stabilized. Ethylenevinyl acetate copolymers are protected, as are butene-methylacrylate copolymers. Nitrogen-containing polymers such as polyurethanes, nitrile rubber, and lauryl acrylate-vinyl -pyrrolidone copolymers are effectively stabilized. Adhesive compositions such as solutions of polychloroprene (neoprene) in toluene are protected.

Petroleum oils such as solvent-refined, midcontinent lubricating oil and Gulf Coast lubricating oils are effectively stabilized. In hydrocarbon lubricating oils, both mineral and synthetic, the present additives may be used in combination with a zinc dihydrocarbyldithiophosphate, e.g. zinc dialkyldithiophosphate or zinc dialkaryldithiophosphate.

The antioxidants of the present invention may be used with mineral oils whether obtained by solvent refining, hydrotreating, hydrocracking, or another method. Thus the antioxidants of the present invention are suitable for combination with a mineral oil of lubricating viscosity which is derived from a lubricating oil produced by contacting a hydrocarbon feedstock with hydrogen preferably in the presence of catalyst effective to promote hydrocracking, at hydrocarbon hydrocracking conditions to produce an oil of lubricating viscosity having an increased viscosity index relative to the viscosity index of the hydrocarbon feedstock.

Typical applications of the antioxidant additives of this invention in oils include use in all motor oils, crankcase oil, turbine oil, diesel oil, industrial oil, hydraulic fluids and the like.

The antioxidant additives of the invention are also useful in fuels including, but not limited to gasoline, alcohol, and the like.

Synthetic ester lubricants such as those used in turbines and turbojet engines may be stabilized. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) may be stabilized. Polyalkylene oxides such as copolymers of phenol with ethylene oxide or propylene oxide may be stabilized. Polyphenyl ethers such as poly-2,6-dimethylphenyl ether formed by polymerization of 2,6-dimethylphenol using a copper-pyridine catalyst may be stabilized. Polycarbonate plastics and other polyformaldehydes may also be protected.

Linear polyesters such as phthalic anhydride-glycol condensates may be given a high degree of protection. Other polyesters such as trimellitic acid-glycerol condensates may also be protected. Polyacrylates such as polymethylacrylate and polymethylmethacrylate may be stabilized. Polyacrylonitriles and copolymers of acrylonitriles with other olefinically unsaturated monomers such as methylmethacrylates may also be effectively stabilized.

The additives can be used to protect any of the many organic substrates to which an antioxidant is normally added. It can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethylsilicone lubricants, phosphate lubricants such as tricresylphosphate, and the like.

The additives are incorporated into the organic substrate in a small but effective amount so as to provide the required antioxidant protection. A useful range is from about 0.005 to about 10 weight percent, and a preferred range is from about 0.05 to 5 weight percent.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with the additive or with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cispolybutadiene or isoprene polymers are blended with the antioxidant together with the other ingredients normally added such as carbon clack, oil, sulfur, zinc oxide, stearic acid, vulcanization accelerators, and the like. Following mastication, the resultant mixture is fabricated and molded into a finished form and vulcanized.

The compounds of structure I of the invention are also usable in the polyurethane arts, in particular for the preparation of polyurethanes by any of various methods including reaction injection molding (RIM), casting of elastomers, and spraying of elastomeric polyurethane coatings. According to the invention, various organic polyisocyanates are usable to form polyurethanes with the compounds of structure I of the invention. These include the 4,4'-methylenebis(phenylisocyanate) (MDI) which is a preferred diisocyanate for preparing RIM polyurethanes. The invention also includes polyurethanes derived from the compounds of structure I with other polyisocyanates such as the following substances and mixtures thereof:

m-phenylenediisocyanates;
2,4-tolunediisocyanates;
2,6-toluenediisocyanates;
naphthalene-1,5-diisocyanates;
1,3,5-benzene-triisocyanates; and
polyarylpolyalkylenepolyisocyanates such as a polymethylenepolyphenolisocyanate.

Isocyanates prepared by phosgenation of the reaction product between aniline and formaldehyde having a functionality of about 2.2 to about 3.5 are known to those skilled in the art.

Polyurethanes of the invention are preferably made from the diols of structure I along with organic polyols. Among the organic polyols are the diols which include, more preferably, the polyether diols predominantly having 2 hydroxy groups bonded to primary carbon atoms. Typically in such more preferred materials up to about 90% of hydroxy groups present are primary. Polyether polyols suitable for use in this invention are made by polymerization of cyclic ethers such as ethylene oxide, propylene oxide, butylene oxide, tetrahydrofuran, and the like. These cyclic ethers can be used individually or as mixtures or in successive fashion when making a polyether.

The organic compounds usable as polyhydroxy reactants for polyurethanes are the dihydroxy polyalkalene polyethers having at least 2 primary hydroxyl groups and a molecular weight of from about 400 to about 12,000, more preferably from about 400 to about 7,000.

Various catalysts including tin catalysts such as dibutyl tin dilaurate are usable according to the invention. U.S. Pat. No. 4,218,543 discloses a variety of catalysts for the RIM process and that patent is incorporated herein by reaerence in its entirety.

Polyurethanes produced by the above described reactants are extended, i.e., chain-lengthened by the compounds of structure I of the invention which react with the isocyanates used in the polyurethane arts. Furthermore, the compounds of the invention are substantially free of groups which react with the isocyanates to terminate a polyurethane chain formation.

The compounds of structure I of the invention are low melting solids at room temperature and are soluble/dispersable in the polyols used in the RIM or other polyurethane processes.

For cast elastomer processes using the compounds of structure I of the invention the polyols are usually of a molecular weight of about 1,000–3,000 and may be of the polyester or polyether type reacted with a stoichiometric excess of diisocyanate to produce a prepolymer. Chain extension is then carried out with the chain extender compound of the structure I compounds of the invention.

Suitable polyester polyols that can be used may be based on polyester glycols such as poly(ethylene adipate), poly(ethylene/propylene adipate), poly(ethylene glutarate), and poly(ethylene pimelate).

Various other components may be added to a polyurethane system using the compounds of structure I of the invention. These include a flame retardant, emulsifiers, foam stabilizers, reaction decelerators such as HCl, dyes, fillers, and the like.

The compounds of structure I of the invention may be made according to the processes of the following non-limiting examples.

EXAMPLE 1

This example demonstrates a method of preparation of one of a variety of precursor ethers of the invention.

Methanol, 440 ml., 48 grams paraformaldehyde, and 6 grams of a 40 percent aqueous solution of dimethylamine are charged to a three-neck round bottom flask and refluxed (about 65° C). A solution of 2,6-diisopropylphenol (178.28 grams—1 mole) in 100 ml. methanol is added dropwise over a period of more than two days. Seven gas chromatography (GC) analyses were taken at representative intervals. They indicated a slow but progressing reaction. After the first GC (one hour) 2.91 grams (0.024 mole) N-methyltoluidine were added. After the fourth GC (21 hours), 5.95 grams (0.05 mole) N-methyltoluidine, 24.87 grams (0.829 mole) paraformaldehyde, and 100 ml. methanol were added while the reaction continued. After 27 hours, 75 ml. methanol and 10.6 grams 40% dimethylamine were distilled off and the refluxing was then continued. At 45 hours, the seventh GC indicated 1.0 area percent 2,6-diisopropylphenol, 35.5 area percent 2,6-diisopropyl-$\alpha$-methoxy-p-cresol; 5.3 area percent 2,6-diisopropyl-$\alpha,\alpha$-dimethoxy-p-cresol; and a small amount of 4,4'-bis(2,6-diisopropylphenol). The reaction product was slightly yellow-brownish in color. The solution was concentrated and the precipitated crystals were filtered and recrystallized from isooctane, given two methanol washings, and dried in vacuum. A GC analysis indicated 95 percent of the desired 2,6-diisopropyl-$\alpha$-methoxy-p-cresol product which was dried in vacuum at room temperature. The yield was 57.4 grams having a melting point of 85.5–86.0. The solvent taken off still contained a large amount of product (very soluble in methanol) some of which precipitated. The residue after distilling off the solvent was crystallized from an oily dark red liquid and filtered off. After washing and recrystallization, another 85.6 grams product were obtained for a total yield of 143 grams (64.4 percent). The structure was confirmed by NMR and GC/mass spectroscopy.

EXAMPLE 2

The following example is a method of preparation of the compounds of the present invention from the precursor ether of Example 1.

Portionwise over a period of about two hours and 15 minutes, 122.54 grams (0.552 mole) of 2,6-diisopropyl-$\alpha$-methoxy-p-cresol (an ether) was added to a mixture of 101.29 grams (0.829 mole) 2,6-dimethylphenol and 114.6 grams of 78 percent sulfuric acid in 690 ml. of methylene chloride. The reaction was carried out at atmospheric pressure and 4°–6° C. under a nitrogen atmosphere with mechanical stirring in a two liter three-neck flask. The temperature was maintained with an ice water bath. Immediately after the eighth of thirteen ether portions had been added, no ether could be detected by gas chromatography analysis (GC), indicating a very fast reaction. After the total addition of the ether, the reaction mixture was allowed to come to room temperature and a second GC indicated no ether present; 90.74 area percent of product phenol, 4-[[4-hydroxy-3,5-bis(1-methylethyl) phenyl]methyl]-2,6-dimethyl; and some dimethylphenol. The mixture was slightly pinkish to yellow-orange. The mixture was transferred to a separatory funnel and rinsed out of the flask with methylene chloride. The heavy sulfuric acid layer was drained off. Water was added and the mixture agitated. Additional methylene chloride was added followed by two 150 ml. water washes.

The methylene chloride and excess 2,6-dimethylphenol was distilled off under vacuum. The viscous liquid product was crystallized in 276 ml. isooctane using seed crystals from a previous run. The product was filtered and rinsed with 50 ml. cold isooctane. The product melting point was only 73°–75° C. and the yield was about 160 grams (about 93 percent).

The various aspects and permutations of the invention may be varied without departing from the scope or spirit of the invention as defined by the following claims.

We claim:

1. A compound of structure I:

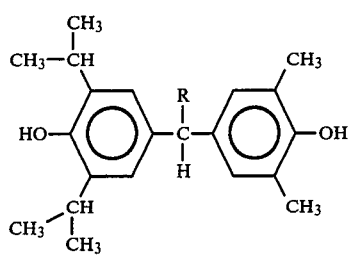 (I)

wherein R is H, alkyl or alkenyl of 1 to 7 carbon atoms, cycloaliphatic of 3 to 7 carbon atoms, aromatic of 6 to 10 carbon atoms, a 5 to 7 member heterocyclic ring, or a heteroatomic radical of 1 to 7 atoms other than H.

2. A compound of claim 1 wherein R is an alkyl of 1 to 7 carbon atoms.

3. A compound of claim 1 wherein R is phenyl.

4. The compound 4-[[4-hydroxy-3,5-bis (1-methylethyl) phyenyl]methyl]-2,6-dimethylphenol:

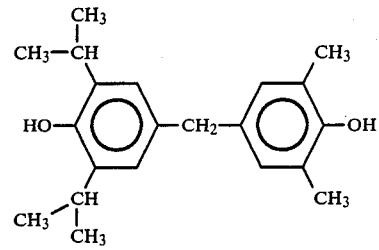

* * * * *

UNITED STATES PATENT AND TRADEMARK OFFICE
CERTIFICATE OF CORRECTION

PATENT NO. : 4,554,389

DATED : NOVEMBER 19, 1985

INVENTOR(S) : KJU HI SHIN, ET AL.

It is certified that error appears in the above-identified patent and that said Letters Patent is hereby corrected as shown below:

Column 6, line 41, reads "carbon clack" and should read -- carbon black --.

Column 6, line 61, reads "2,4-tolunediisocyanates" and should read -- 2,4-toluenediisocyanates --.

Column 7, line 25, reads "reaerence" and should read -- reference --.

Column 10, line 5, reads "phyenyl" and should read -- phenyl --.

Signed and Sealed this

Twenty-fifth Day of February 1986

[SEAL]

Attest:

DONALD J. QUIGG

Attesting Officer

Commissioner of Patents and Trademarks